US012773102B2

(12) United States Patent
Abe et al.

(10) Patent No.: US 12,773,102 B2
(45) Date of Patent: Oct. 27, 2026

(54) LIGHT EMITTING DEVICE; AND MEDICAL SYSTEM, ELECTRONIC APPARATUS, AND INSPECTION METHOD USING SAME

(71) Applicant: Panasonic Intellectual Property Management Co., Ltd., Osaka (JP)

(72) Inventors: Takeshi Abe, Osaka (JP); Shozo Oshio, Osaka (JP); Mitsuru Nitta, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 983 days.

(21) Appl. No.: 17/603,910

(22) PCT Filed: Feb. 19, 2020

(86) PCT No.: PCT/JP2020/006523

§ 371 (c)(1),
(2) Date: Oct. 14, 2021

(87) PCT Pub. No.: WO2020/217670

PCT Pub. Date: Oct. 29, 2020

(65) Prior Publication Data

US 2022/0192477 A1 Jun. 23, 2022

(30) Foreign Application Priority Data

Apr. 24, 2019 (JP) ................................ 2019-082916

(51) Int. Cl.
*A61B 1/04* (2006.01)
*A61B 1/00* (2006.01)
(Continued)

(52) U.S. Cl.
CPC ............. *A61B 1/043* (2013.01); *A61B 1/046* (2022.02); *A61B 1/0653* (2013.01);
(Continued)

(58) Field of Classification Search
CPC ....... A61B 1/043; A61B 1/046; A61B 1/0653; A61B 1/0684; A61B 1/00165;
(Continued)

(56) References Cited

U.S. PATENT DOCUMENTS

2006/0082679 A1 4/2006 Chua
2006/0082995 A1 4/2006 Chua
(Continued)

FOREIGN PATENT DOCUMENTS

CN 107304984 A 10/2017
EP 3904488 A1 11/2021
(Continued)

OTHER PUBLICATIONS

Jiaren Du, Temperature dependent persistent luminescence: Evaluating the optimum working temperature, Jul. 19, 2019.*
(Continued)

*Primary Examiner* — Benjamin J Klein
*Assistant Examiner* — Thien Jason Tran
(74) *Attorney, Agent, or Firm* — Renner, Otto, Boisselle & Sklar LLP

(57) ABSTRACT

A light emitting device includes a light source configured to emit a primary light, a first phosphor that absorbs the primary light and converts the primary light into a first wavelength-converted light having a wavelength longer than that of the primary light, and a second phosphor that absorbs the primary light and converts the primary light into a second wavelength-converted light having a wavelength longer than that of the primary light. The first wavelength-converted light is a fluorescence having a light component over an entire wavelength range of 700 nm or more to 800 nm or less. The second wavelength-converted light is a fluorescence having a peak where a fluorescence intensity shows a maximum value in a wavelength range of 380 nm
(Continued)

or more to less than 700 nm. The first wavelength-converted light has a 1/10 afterglow time longer than that of the second wavelength-converted light.

19 Claims, 6 Drawing Sheets

(51) Int. Cl.

| | |
|---|---|
| ***A61B 1/06*** | (2006.01) |
| ***C01G 15/00*** | (2006.01) |
| ***C09K 11/77*** | (2006.01) |
| ***H10H 20/851*** | (2025.01) |
| *B82Y 20/00* | (2011.01) |
| *B82Y 40/00* | (2011.01) |
| *H10K 102/00* | (2023.01) |

(52) U.S. Cl.
CPC .......... *A61B 1/0684* (2013.01); *C01G 15/006* (2013.01); *C09K 11/7701* (2013.01); *C09K 11/7721* (2013.01); *H10H 20/8513* (2025.01); *B82Y 20/00* (2013.01); *B82Y 40/00* (2013.01); *C01P 2002/70* (2013.01); *C01P 2004/64* (2013.01); *C01P 2006/60* (2013.01); *H10K 2102/00* (2023.02)

(58) Field of Classification Search
CPC ... A61B 1/00186; A61B 1/042; A61B 1/0669; C01G 15/006; C09K 11/7701; C09K 11/7721; C09K 11/7708; H01L 33/504; B82Y 20/00; B82Y 40/00; C01P 2002/70; C01P 2004/64; C01P 2006/60; H10K 2102/00; H01S 5/0087
See application file for complete search history.

(56) References Cited

U.S. PATENT DOCUMENTS

2008/0033300 A1* 2/2008 Hoang .................. A61B 18/20 606/42
2008/0231170 A1* 9/2008 Masato ............. C09K 11/7789 430/23
2015/0226389 A1* 8/2015 Kasugai .................... F21K 9/64 353/31
2016/0276549 A1* 9/2016 Yamashita ........... G02B 6/0091
2016/0287081 A1 10/2016 Yang
2017/0213942 A1* 7/2017 Takehara ........... H10H 20/8513
2017/0236281 A1* 8/2017 Dacosta ................ G06T 7/0016 382/128
2017/0283261 A1* 10/2017 Hirosaki .............. C09K 11/643
2017/0307968 A1 10/2017 Nagasaki et al.
2018/0120157 A1 5/2018 Kaufmann
2018/0358514 A1 12/2018 Tragl
2019/0256769 A1* 8/2019 Jia .................... C09K 11/77062
2020/0010760 A1 1/2020 Ueda et al.
2020/0048549 A1 2/2020 Hong

FOREIGN PATENT DOCUMENTS

JP 2006-114911 A 4/2006
JP 2007-17986 A 1/2007
JP 2013-239551 A 11/2013
JP 2018-515913 A 6/2018
JP 2018-518046 A 7/2018
JP 6461411 B1 1/2019
WO 2018/143198 A1 8/2018
WO 2018/163830 A1 9/2018
WO 2018/207703 A1 11/2018

OTHER PUBLICATIONS

Extended European Search Report for corresponding EP Application No. 20794717.7 issued Jun. 7, 2022.
S. Ye, et al., "Broadband Cr3+-sensitized upconversion luminescence in La3Ga5GeO14: Cr3+, Yb3+, Er3+", Optical Materials Express, Mar. 7, 2014, vol. 4, No. 4, p. 638-648.
Akihiro Yamaji, et al., "Luminescence Properties of Gd3Ga5012:Cr Single Crystals", IEEE Transactions on Nuclear Science, Jan. 9, 2014, vol. 61, No. 1, p. 320-322.
Ya. Zakharko, et al., "Optical Absorption and Luminescence of Gd3Ga5O12:Cr, Mg Epitaxial Films", Acta Physica Polonica A, 2010, vol. 117, No. 1, p. 111-113.
P. I. Macfarlane, et al., "Cr3+ luminescence in calcium and strontium gallogermanate", Optical Materials, Feb. 1994, vol. 3, No. 1, p. 15-24.
International Search Report for corresponding Application No. PCT/JP2020/006523, mailed Apr. 28, 2020.
Written Opinion for corresponding Application No. PCT/JP2020/006523, mailed Apr. 28, 2020.

* cited by examiner

LIGHT EMITTING DEVICE; AND MEDICAL SYSTEM, ELECTRONIC APPARATUS, AND INSPECTION METHOD USING SAME

TECHNICAL FIELD

The present invention relates to a light emitting device, and a medical system, an electronic apparatus, and an inspection method using the light emitting device.

BACKGROUND

A method of observing lesions, called a fluorescence imaging method, has been attracting attention recently in the medical field. The fluorescence imaging method is a method of observing a lesion by administering a fluorescent drug that selectively binds to the lesion such as a tumor to a subject, exciting the fluorescent drug with a specific light, and detecting and imaging fluorescence emitted from the fluorescent drug by an image sensor. The fluorescence imaging method makes it possible to observe lesions that are difficult to observe visually.

As a typical fluorescence imaging method, a fluorescence imaging method (ICG fluorescence method) using indocyanine green (ICG) as a fluorescent drug is known. The ICG is excited by a near-infrared light (for example, fluorescence peak wavelength is 770 nm), which easily penetrates a living body, and emits a near-infrared light of a longer wavelength (for example, fluorescence peak wavelength is 810 nm). Therefore, by detecting the fluorescence emitted from the ICG, observation of a lesion inside the living body is possible. The ICG fluorescence method is a minimally invasive medical technology that achieves the observation of lesions inside the living body without damaging the living body.

The fluorescence imaging method, such as the ICG fluorescence method, uses at least a device that emits a near-infrared light. As an optoelectronic element emitting near-infrared fluorescence, Patent Literature 1 discloses an optoelectronic element that includes a semiconductor chip emitting a primary beam and a conversion material including $Cr^{3+}$ ions and/or $Ni^{2+}$ ions.

CITATION LIST

Patent Literature

PTL1: Japanese Translation of PCT International Application Publication No. JP-T-2018-518046

SUMMARY

As described above, to utilize a fluorescence imaging method, such as the ICG fluorescence method, at least a device for emitting near-infrared light is used. In contrast, to normally visually observe the state of a mucosal surface layer through an image projected by an image sensor for visible light or through a lens, it is preferable that visible light is also emitted. Therefore, if a device for simultaneously emitting visible light and near-infrared light is provided, it is possible to achieve both normal observation using visible light and special observation using near-infrared light.

However, when mixed light of visible light and near-infrared light is emitted, a light component of the visible light, which is closer to the near-infrared range, is easily detected by the near-infrared light image sensor. Therefore, a light component other than the near-infrared fluorescence emitted from, for example, a fluorescent drug, is also detected by the near-infrared light image sensor to generate noise, and it is difficult to observe the lesion with high contrast.

The present invention has been made in consideration of such an issue as described above. It is an object of the present invention to provide a light emitting device that emits near-infrared light and visible light to obtain a high-contrast observation result, and a medical system, an electronic apparatus, and an inspection method using the light emitting device.

In response to the above issue, a light emitting device according to a first aspect of the present invention includes: a light source configured to emit a primary light; a first phosphor that absorbs the primary light and converts the primary light into a first wavelength-converted light having a wavelength longer than that of the primary light; and a second phosphor that absorbs the primary light and converts the primary light into a second wavelength-converted light having a wavelength longer than that of the primary light. The first wavelength-converted light is a fluorescence having a light component over an entire wavelength range of 700 nm or more to 800 nm or less. The second wavelength-converted light is a fluorescence having a peak where a fluorescence intensity shows a maximum value in a wavelength range of 380 nm or more to less than 700 nm. The first wavelength-converted light has a 1/10 afterglow time longer than that of the second wavelength-converted light.

A medical system according to a second aspect of the present invention includes the light emitting device according to the first aspect.

An electronic apparatus according to a third aspect of the present invention includes the light emitting device according to the first aspect.

An inspection method according to a fourth aspect of the present invention uses the light emitting device according to the first aspect.

DESCRIPTION OF EMBODIMENTS

Figure 1:
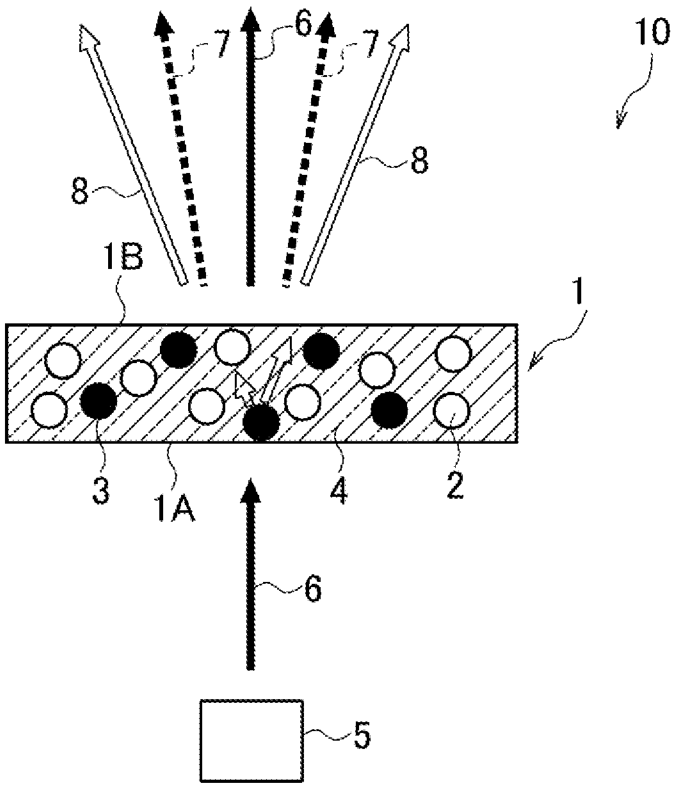
FIG. 1 is a schematic sectional view of an example of a light emitting device according to a present embodiment.

A detailed description is given below of a light emitting device, and a medical system, an electronic apparatus, and an inspection method using the light emitting device according to a present embodiment. Note that dimensional ratios in the drawings are exaggerated for convenience of explanation, and are sometimes different from actual ratios.

[Light Emitting Device]

A light emitting device 10 according to the present embodiment is described below with reference to FIGS. 1 to 6.

As illustrated in FIG. 1, a light emitting device 10 according to the present embodiment includes a light source 5, and a wavelength converter 1. The wavelength converter 1 includes a first phosphor 2 and a second phosphor 3. That is the light emitting device 10 includes the light source 5, the first phosphor 2, and the second phosphor 3. The light source 5 emits a primary light 6. The first phosphor 2 absorbs the primary light 6 and converts it into a first wavelength-converted light 7 having a wavelength longer than that of the primary light 6. The second phosphor 3 absorbs the primary light 6 and converts it into a second wavelength-converted light 8 having a wavelength longer than that of the primary light 6.

The first wavelength-converted light 7 is a fluorescence having a light component over the entire wavelength range of 700 nm or more to 800 nm or less. The second wavelength-converted light 8 is a fluorescence having a peak where the fluorescence intensity shows a maximum value in a wavelength range of 380 nm or more to less than 700 nm. The first wavelength-converted light 7 has 1/10 afterglow time longer than that of the second wavelength-converted light 8. Note that the 1/10 afterglow time means time $\tau_{1/10}$ taken from the time when the maximum light emission intensity is shown to the time when the intensity becomes 1/10 of the maximum light emission intensity.

Figure 2:
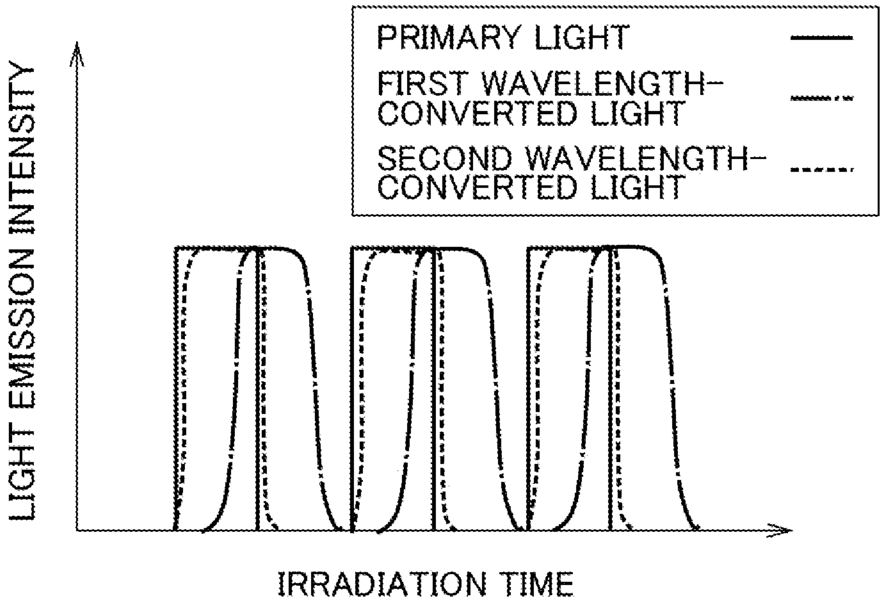
FIG. 2 is a graph illustrating an image of a relationship between irradiation time and light emission intensity for a primary light, a first wavelength-converted light, and a second wavelength-converted light.

FIG. 2 is a graph of an image of a relationship between irradiation time and light emission intensity for the primary light 6, the first wavelength-converted light 7, and the second wavelength-converted light 8. The light emission intensity of each light in FIG. 2 is graphed so that the value of the maximum light emission intensity is the same. As illustrated in FIG. 2, when the light source 5 is turned on, the light source 5 is on, and the primary light 6 is emitted by the light source 5. When the primary light 6 emitted by the light source 5 is emitted to the wavelength converter 1, the second wavelength-converted light 8 including visible light is emitted from the second phosphor 3 immediately after the primary light 6 is emitted. The first wavelength-converted light 7 including a near-infrared fluorescence is emitted after the emission of the second wavelength-converted light 8. In contrast, when the power of the light source 5 is turned off, the light source 5 is off, and the primary light 6 is no longer emitted by the light source 5, the light emission intensity of the second wavelength-converted light 8 becomes 1/10 of the maximum light emission intensity. The first wavelength-converted light 7 continues to maintain a predetermined light emission intensity while attenuating, and after the light emission intensity of the second wavelength-converted light 8 becomes 1/10 of the maximum light emission intensity, the light emission intensity of the first wavelength-converted light 7 becomes 1/10 of the maximum light emission intensity.

Therefore, immediately after the primary light 6 is emitted to the first phosphor 2 and the second phosphor 3, the second wavelength-converted light 8 is relatively predominantly emitted, and for a predetermined period after the primary light 6 is no longer emitted by the light source 5, the first wavelength-converted light 7 is relatively predominantly emitted. As a result, the light emitting device 10 emits alternately in time a near-infrared fluorescent component having excellent living body permeability, a wide fluorescence spectrum width, and a long afterglow property, and a visible fluorescent component having a large proportion of light components having excellent visibility and a short afterglow property.

The near-infrared fluorescent component excites, for example, a fluorescent drug used in a fluorescence imaging method, so that the fluorescent drug emits a near-infrared fluorescence having a wavelength longer than that of the exciting near infrared. The near-infrared fluorescence emitted by the fluorescent drug is detected and imaged by a near-infrared light image sensor, and thus special observation is possible. In contrast, the visible fluorescent component emitted by the light emitting device 10 is useful for normal visual observation of a diseased part of a living body.

The light emitting device 10 according to the present embodiment emits alternately in time the near-infrared fluorescent component and the visible fluorescent component. Thus, the near-infrared fluorescence image sensor detects the near-infrared fluorescence component having a relatively high intensity ratio while the intensity of the noise component is relatively low. Accordingly, the light emitting device 10 emits the near-infrared light and the visible light by utilizing the afterglow time difference to obtain a high-contrast observation result.

As described above, the first phosphor 2 absorbs the primary light 6 and converts it into the first wavelength-converted light 7 having a wavelength longer than that of the primary light 6. However, the first phosphor 2 may be a phosphor that absorbs not only the primary light 6 but also the second wavelength-converted light 8 and emits the first wavelength-converted light 7. That is, the second phosphor 3 may be excited by the primary light 6 to emit the second wavelength-converted light 8, and the first phosphor 2 may be excited by the second wavelength-converted light 8 to emit the first wavelength-converted light 7. In this case, even if the first phosphor 2 is a phosphor that is hardly excited by the primary light 6, it is possible to excite the first phosphor 2 by the fluorescence emitted by the second phosphor 3. As a result, a phosphor that absorbs visible light is selectable as the first phosphor 2, which expands the choice of the first phosphor 2 and facilitates the industrial production of the light emitting device 10. When the first phosphor 2 absorbs the second wavelength-converted light 8 and emits the first wavelength-converted light 7, the light emitting device 10 is capable of emitting the first wavelength-converted light 7 having a large near-infrared light component intensity.

Preferably, the primary light 6 is a laser light. The laser light is a high-output point light source with strong directivity, and thus it not only reduces the size of the optical system and the diameter of the light guiding part but also improves the coupling efficiency of the laser light to an optical fiber. Accordingly, the light emitting device 10 that facilitates high output is obtained. Preferably, the laser light is emitted by a semiconductor light emitting device from the viewpoint of miniaturization of the light emitting device 10.

Preferably, the primary light 6 is a continuous pulsed light. In this way, immediately after the pulsed light is turned off, the first wavelength-converted light 7 having a near-infrared fluorescent component emits phosphorescence longer than the second wavelength-converted light 8 that becomes visible light. By utilizing the phosphorescence component as the excitation light of the above-described drug, only the near-infrared fluorescent component emitted by the drug enters the image sensor, and the second wavelength-converted light 8 hardly enters the image sensor. Accordingly, the light emitting device 10 advantageous for the improvement of the S/N ratio of the near-infrared fluorescent component emitted by the drug is obtained. Preferably, the pulse wave of the pulsed light is a square wave. This makes it easy for the image sensor to detect only the near-infrared fluorescence emitted by the drug, and thus it is possible to improve the S/N ratio of the near-infrared fluorescence emitted by the drug.

When the primary light 6 is a continuous pulsed light, preferably, the extinction time of the continuous pulsed light is longer than the 1/10 afterglow time of the second wavelength-converted light 8. This increases the time during which the intensity of the second wavelength-converted light 8 is relatively small and the intensity of the near-infrared fluorescence emitted by the drug is relatively high. As a result, only the near-infrared fluorescence emitted by the drug is easily detected by the image sensor, and thus the S/N ratio of the near-infrared fluorescence emitted by the drug is improved.

The duty ratio of the continuous pulsed light is preferably 0.01% or more and 50% or less, preferably 0.1% or more and 20% or less. Setting the duty ratio in the above range shortens the time during which the visible light and the near-infrared light are simultaneously emitted and lengthens the time during which the intensity of the visible light or the near-infrared light is relatively high. Therefore, the light emitting device 10 according to the present embodiment provides observation results with higher contrast.

The lighting time (that is, the pulse width) of the continuous pulsed light is preferably 0.1 μs or more and 0.1 s or less, more preferably 1 μs or more and 50 ms or less. Setting the lighting time in such a range sufficiently secures a time when the intensity of the visible light is relatively high. In contrast, the extinction time of the continuous pulsed light is preferably 0.1 μs or more and 0.5 s or less, more preferably 0.5 μs or more and 0.3 s or less, still more preferably 10 μs or more and 0.1 s or less. Setting the lights-out time in such a range sufficiently secures a time when the intensity of the near-infrared light is relatively high.

Preferably, the spectrum of the light emitted by the light source 5 has a peak where the intensity shows a maximum value in a range of 400 nm or more to less than 500 nm. Also preferably, the spectrum of the light emitted by the light source 5 has a peak where the intensity shows a maximum value in a wavelength range of 420 nm or more to less than 480 nm, and the light emitted by the light source 5 is blue light. The spectrum of the light emitted by the light source 5 has a peak where the intensity shows a maximum value more preferably in a wavelength range of 430 nm or more to less than 480 nm, even more preferably in a wavelength range of 440 nm or more to less than 470 nm. Thus, the first phosphor 2 and the second phosphor 3 are excited with high efficiency, which enables the light emitting device 10 to emit high-output near-infrared light.

The light source 5 may include a red laser device. The light source 5 may include a blue laser device. The red laser device has a small energy difference from the near-infrared light component and a small energy loss associated with wavelength conversion, which is preferable in achieving high efficiency of the light emitting device 10. In contrast, a laser device with high efficiency and high output is easily available for the blue laser device, and thus the blue laser device is preferable in achieving high output of the light emitting device 10. Preferably, the light source 5 includes a blue laser device as an excitation source and emits blue laser light. Thus, the first phosphor 2 and the second phosphor 3 are excited with high efficiency and high output, which enables the light emitting device 10 to emit high-output near-infrared light.

Preferably, the light source 5 includes a solid-state light emitting device, and the above-described blue light is emitted by the solid-state light emitting device. In this way, a small-sized light emitting device with high reliability is used as a light emitting source of the above-described blue light, which provides a small-sized light emitting device 10 with high reliability.

The solid-state light emitting device is a light emitting device that emits the primary light 6. Any solid-state light emitting device is usable as long as it emits the primary light 6 with a high energy density. The solid-state light emitting device is preferably at least one of a laser device or a light-emitting diode (LED), more preferably a laser device. The light source 5 may be, for example, a surface emitting laser diode.

The rated light output of the solid-state light emitting device is preferably 1 W or more, more preferably 3 W or more. This enables the light source 5 to emit the primary light 6 with high output, and thus the light emitting device 10 that facilitates high output is obtained.

The upper limit of the rated light output is not limited, and the rated light output is increased by the light source 5 having a plurality of solid-state light emitting devices. However, for practical purposes, the rated light output is preferably less than 10 kW, more preferably less than 3 kW.

The light density of the primary light 6 is preferably more than 0.5 $W/mm^2$, more preferably more than 3 $W/mm^2$, still more preferably more than 10 $W/mm^2$. The light density may exceed 30 $W/mm^2$. In this way, the first phosphor 2 and the second phosphor 3 are photoexcited at high density, which enables the light emitting device 10 to emit a fluorescent component of high output.

Preferably, the correlated color temperature of the second wavelength-converted light 8 is 2500 K or more and less than 7000 K. The correlated color temperature is more preferably 2700 K or more and less than 5500 K, more preferably 2800 K or more and less than 3200 K or 4500 K or more and less than 5500 K. The output light with a correlated color temperature within the above-described range is a white output light, and a diseased part visible through an image display device or an optical device appears similar to the diseased part observed under natural light. Therefore, the light emitting device 10 is obtained that easily makes use of the medical experience of doctors, which is preferable for medical use.

Preferably, the second wavelength-converted light 8 has a light component over the entire wavelength range of 500 nm or more to less than 580 nm. Since the second wavelength-converted light 8 has such a light component, the light emitting device 10 effectively emits a fluorescent component advantageous for visual inspection. The second wavelength-converted light 8 may have a light component over the entire wavelength range of 500 nm or more to less than 600 nm.

The first wavelength-converted light 7 has a light component over the entire wavelength range of 700 nm or more to 800 nm or less. More preferably, the first wavelength-converted light 7 has a light component over the entire wavelength range of 750 nm or more to 800 nm or less. This enables the light emitting device 10 to emit a near-infrared excitation light that efficiently excites a drug, even when the drug has a near-infrared light absorption property that is likely to vary. Thus, the light emitting device 10 increases the amount of near-infrared light emitted from a fluorescent drug, or heat rays emitted from a photosensitive drug.

The first phosphor 2 is preferably activated with a transition metal ion, more preferably activated with $Cr^{3+}$. This makes it easy to obtain a near-infrared fluorescence having a wide fluorescence spectrum width and a long afterglow of 100 μs or more, as the first wavelength-converted light 7.

Preferably, the first wavelength-converted light 7 includes a fluorescence based on the electronic energy transition of $Cr^{3+}$. Preferably, the fluorescence spectrum of the first wavelength-converted light 7 has a peak where the fluorescence intensity shows a maximum value in a wavelength range exceeding 720 nm. This enables the first phosphor 2 to emit a fluorescence in which a broad spectral component of a short afterglow property is more dominant than a linear spectral component of a long afterglow property. As a result, the light emitting device 10 emits a light including a large number of near-infrared components. The linear spectrum component is a fluorescence component based on the electron energy transition (spin-forbidden transition) of $^2E \rightarrow {}^4A_2(t_2^3)$ of $Cr^{3+}$ and has a peak where the fluorescence intensity shows a maximum value in a wavelength range of 680 nm to 720 nm. The broad spectral component is a fluorescence component based on the electron energy transition (spin-allowed transition) of $^4T_2(t_2^2e) \rightarrow {}^4A_2(t_2^3)$ of $Cr^{3+}$ and has a peak where the fluorescence intensity shows a maximum value in a wavelength range exceeding 720 nm.

The fluorescence spectrum of the first wavelength-converted light 7 may have a peak where the fluorescence intensity shows a maximum value in a wavelength range of 710 nm or more to 900 nm or less. The fluorescence spectrum of the first wavelength-converted light 7 more preferably has a peak where the fluorescence intensity shows a maximum value in a wavelength range exceeding 730 nm, further more preferably has a peak where the fluorescence intensity shows a maximum value in a wavelength range exceeding 750 nm.

The 1/10 afterglow time of the first wavelength-converted light 7 is preferably less than 1 ms, more preferably less than 300 μs, still more preferably less than 100 μs. Thus, even when the light density of the excitation light for exciting the first phosphor 2 is high, the output of the first wavelength-converted light 7 hardly saturates. Therefore, the light emitting device 10 capable of emitting a high output near-infrared light is obtained.

Preferably, the 1/10 afterglow time of the first wavelength-converted light 7 is longer than the 1/10 afterglow time of the second wavelength-converted light 8. Preferably the 1/10 afterglow time of the first wavelength-converted light 7 is specifically 10 us or more. Note that the 1/10 afterglow time of the first wavelength-converted light 7 activated with $Cr^{3+}$ is longer than the 1/10 afterglow time of a short afterglow (less than 10 μs) fluorescence based on a parity-allowed transition of $Ce^{3+}$, $Eu^{2+}$, or the like. This is because the first wavelength-converted light 7 is a fluorescence based on the electron energy transition of the spin-allowed type of $Cr^{3+}$, which has relatively long afterglow time.

The 1/10 afterglow time difference between the first wavelength-converted light 7 and the second wavelength-converted light 8 is preferably more than 50 μs, more preferably more than 100 μs. The 1/10 afterglow time difference is a difference between the 1/10 afterglow time of the first wavelength-converted light 7 and the 1/10 afterglow time of the second wavelength-converted light 8. Thus, when the light source 5 is turned off, even if the intensity of the fluorescent component of the visible light emitted by the second phosphor 3 as a main component greatly decreases, the intensity of the fluorescent component of the near infrared emitted by the first phosphor 2 as a main component remains relatively high. This enables special observation using the near-infrared light emitted by the drug to be compatible with normal observation using the visible light. Preferably, the 1/10 afterglow time difference is less than 1 ms.

Preferably, in the fluorescence spectrum of the first wavelength-converted light 7, the spectral width at an intensity of 80% of the maximum value of the fluorescence intensity is 20 nm or more and less than 80 nm. Thus, the main component of the first wavelength-converted light 7 becomes a broad spectrum component. Therefore, even when there is a variation in the wavelength dependence of the sensitivity of a fluorescent drug or photosensitive drug in a medical field using a fluorescence imaging method or photodynamic therapy (PDT method), the light emitting device 10 emits high output near-infrared light that enables these drugs to function sufficiently.

Preferably, in the fluorescence spectrum of the first wavelength-converted light 7, the ratio of the fluorescence intensity at a wavelength of 780 nm to the maximum fluorescence intensity exceeds 30%. The ratio of the fluorescence intensity at a wavelength of 780 nm to the maximum fluorescence intensity more preferably exceeds 60%, even more preferably exceeds 80%. This enables the first phosphor 2 to emit a fluorescence including a large number of fluorescent components of a near-infrared wavelength range (650 to 1000 nm) through which light easily penetrates the living body, which is called a "living body window". Therefore, the above-described light emitting device 10 increases the light intensity of the near infrared that penetrates the living body.

Preferably, the fluorescence spectrum of the first wavelength-converted light 7 does not leave a trail of a linear spectral component derived from the electronic energy transition of $Cr^{3+}$. That is, preferably, the first wavelength-converted light 7 has only a broad spectral component (short afterglow property) having a peak where the fluorescence intensity shows a maximum value in a wavelength range exceeding 720 nm. Thus, the first phosphor 2 does not include a long afterglow fluorescent component due to the spin-forbidden transition of $Cr^{3+}$ but only includes a short afterglow fluorescent component due to the spin-allowed transition of $Cr^{3+}$. Thus, even when the light density of the excitation light for exciting the first phosphor 2 is high, the output of the first wavelength-converted light 7 hardly saturates. Therefore, the light emitting device 10 of a point light source capable of emitting a near-infrared light of higher output is also obtained.

Preferably, the first phosphor 2 includes no activator other than $Cr^{3+}$. This enables the light absorbed by the first phosphor 2 to be converted into only the fluorescence based on the electronic energy transition of $Cr^{3+}$, which provides the light emitting device 10 with easy design of output light for maximizing the output ratio of the near-infrared fluorescent component.

Preferably, the first phosphor 2 includes two or more kinds of $Cr^{3+}$-activated phosphors. This enables the output light component in at least the near-infrared wavelength range to be controlled, which provides the light emitting device 10 with easy adjustment of the spectral distribution in accordance with the application utilizing the near-infrared fluorescence component.

The first phosphor 2 is preferably an oxide-based phosphor, more preferably an oxide phosphor. The oxide-based phosphor means a phosphor including oxygen but not nitrogen.

Since the oxide is stable in the atmosphere, even when the oxide phosphor generates heat due to high density photoexcitation by laser light, it is difficult for phosphor crystals to be altered by oxidation in the atmosphere, as occurs in nitride phosphors. Therefore, when all the phosphors in the wavelength converter 1 are oxide phosphors, the light emitting device 10 that is highly reliable is obtained.

Preferably, the first phosphor 2 has a garnet crystal structure. Preferably, the first phosphor 2 is an oxide phosphor with a garnet crystal structure. Since a garnet phosphor is easily deformed in composition and provides a number of phosphor compounds, a crystal field around $Cr^{3+}$ is easily adjusted, and the color tone of fluorescence based on the electronic energy transition of $Cr^{3+}$ is easily controlled.

The phosphor with a garnet structure, especially the oxide, has a polyhedral particle shape close to a sphere and has excellent dispersibility of a phosphor particle group. Therefore, when the phosphor included in the wavelength converter 1 has a garnet structure, the wavelength converter 1 excellent in light transmittance is manufactured relatively easily, which enables higher output of the light emitting device 10. Further, since a phosphor with a garnet crystal structure has practical experience as a phosphor for LEDs, the light emitting device 10 that is a highly reliable is obtained when the first phosphor 2 has the garnet crystal structure.

The first phosphor 2 may include at least one phosphor selected from the group consisting of: $Lu_2CaMg_2(SiO_4)_3$:$Cr^{3+}$, $Y_3Ga_2(AlO_4)_3$:$Cr^{3+}$, $Y_3Ga_2(GaO_4)_3$:$Cr^{3+}$, $Gd_3Ga_2(AlO_4)_3$:$Cr^{3+}$, $Gd_3Ga_2(GaO_4)_3$:$Cr^{3+}$, $(Y,La)_3Ga_2(GaO_4)_3$:$Cr^{3+}$, $(Gd,La)_3Ga_2(GaO_4)_3$:$Cr^{3+}$, $Ca_2LuZr_2(AlO_4)_3$:$Cr^{3+}$, $Ca_2GdZr_2(AlO_4)_3$:$Cr^{3+}$, $Lu_3Sc_2(GaO_4)_3$:$Cr^{3+}$, $Y_3Sc_2(AlO_4)_3$:$Cr^{3+}$, $Y_3Sc_2(GaO_4)_3$:$Cr^{3+}$, $Gd_3Sc_2(GaO_4)_3$:$Cr^{3+}$, $La_3Sc_2(GaO_4)_3$:$Cr^{3+}$, $Ca_3Sc_2(SiO_4)_3$:$Cr^{3+}$, $Ca_3Sc_2(GeO_4)_3$:$Cr^{3+}$, $BeAl_2O_4$:$Cr^{3+}$, $LiAl_5O_8$:$Cr^{3+}$, $LiGa_5O_8$:$Cr^{3+}$, $Mg_2SiO_4$:$Cr^{3+}$, $Li^+$, $La_3Ga_5GeO_{14}$:$Cr^{3+}$, and $La_3Ga_{5.5}Nb_{0.5}O_{14}$:$Cr^{3+}$.

As described above, the first wavelength-converted light 7 has a near-infrared fluorescence component. This enables the light emitting device 10 to efficiently excite a fluorescent drug, such as ICG, or a photosensitive drug (which is also a fluorescent drug), such as phthalocyanine.

Preferably, the second phosphor 3 is activated with at least one of $Ce^{3+}$ or $Eu^{2+}$. This makes it easy to obtain the second wavelength-converted light 8 including a large number of visible lights having a short afterglow of less than 10 Preferably, the second phosphor 3 is a phosphor activated with $Ce^{3+}$.

The second phosphor 3 may be at least one of an oxide-based phosphor, such as an oxide or a halogen oxide, or a nitride-based phosphor, such as a nitride or an oxynitride.

Preferably, the second phosphor 3 is a $Ce^{3+}$-activated phosphor having a matrix of a compound with at least one, as a main component, selected from the compound group consisting of a garnet type crystal structure, a calcium ferrite type crystal structure, and a lanthanum silicon nitride ($La_3Si_6N_{11}$) type crystal structure. Preferably, the second phosphor 3 is a $Ce^{3+}$-activated phosphor having a matrix of at least one selected from the compound group consisting of a garnet type crystal structure, a calcium ferrite type crystal structure, and a lanthanum silicon nitride ($La_3Si_6N_{11}$) type crystal structure. Using the above-described second phosphor 3 provides output light with a large number of light components from green to yellow.

Preferably, the second phosphor 3 is specifically a $Ce^{3+}$-activated phosphor having a matrix of a compound with at least one, as a main component, selected from the group consisting of $M_3RE_2(SiO_4)_3$, $RE_3Al_2(AlO_4)_3$, $MRE_2O_4$, and $RE_3Si_6N_{ii}$. Preferably, the second phosphor 3 is a $Ce^{3+}$-activated phosphor having a matrix of at least one selected from the group consisting of $M_3RE_2(SiO_4)_3$, $RE_3Al_2(AlO_4)_3$, $MRE_2O_4$, and $RE_3Si_6N_{11}$. Preferably, the second phosphor 3 is a $Ce^{3+}$-activated phosphor having a matrix of a solid solution having the above-described compound as an end component. Note that M is an alkaline earth metal, and RE is a rare earth element.

The above-described second phosphor 3 well absorbs light in a wavelength range of 430 nm or more to 480 nm or less and converts it to green to yellow light with a peak where the fluorescence intensity shows a maximum value in a wavelength range of 540 nm or more to less than 590 nm with high efficiency. Therefore, a visible light component is easily obtained by using such a phosphor as the second phosphor 3 with the light source 5 that emits cold color light in a wavelength range of 430 nm or more to 480 nm or less as the primary light 6.

Preferably, the wavelength converter 1 includes an inorganic material. Here, the inorganic material means materials other than organic materials and includes ceramics and metals as a concept. When the wavelength converter 1 includes an inorganic material, the wavelength converter 1 has the heat conductivity higher than that of the wavelength converter including an organic material, such as a sealing resin, thereby facilitating the heat radiation design. Thus, the temperature rise of the wavelength converter 1 is effectively prevented even when the phosphor is photoexcited with high density by the primary light 6 emitted from the light source 5. As a result, the temperature quenching of the phosphor in the wavelength converter 1 is prevented, and thus higher output of light emission is possible. Accordingly, the heat dissipation of the phosphor is improved, and thus the decrease in output of the phosphor due to temperature quenching is prevented, and high output near-infrared light is emitted.

Preferably, all of the wavelength converter 1 is made of an inorganic material. As a result, the heat dissipation of the first phosphor 2 and the second phosphor 3 is improved, and thus the decrease in output of the phosphor due to temperature quenching is prevented, and the light emitting device 10 that emits a high output near-infrared light is obtained.

At least one of the first phosphor 2 or the second phosphor 3 may be a ceramic. This increases the thermal conductivity of the wavelength converter 1, which provides the light emitting device 10 with less heat generation and high output. Here, the ceramic means a sintered body in which particles are bonded to each other.

As illustrated in FIG. 1, preferably, the wavelength converter 1 further includes a sealing material 4 that disperses the first phosphor 2 and the second phosphor 3, in addition to the first phosphor 2 and the second phosphor 3. Preferably, the wavelength converter 1 has the first phosphor 2 and the second phosphor 3 dispersed in the sealing material 4. By dispersing the first phosphor 2 and the second phosphor 3 in the sealing material 4, the light emitted to the wavelength converter 1 is efficiently absorbed and wavelength-converted into a near-infrared light. Further, the wavelength converter 1 is easily formed into a sheet shape or a film shape.

Preferably, the sealing material 4 is at least one of an organic material or an inorganic material, particularly at least one of a transparent (light transmitting) organic material or a transparent (light transmitting) inorganic material. Examples of the sealing material of the organic material include a transparent organic material, such as a silicone resin. Examples of the sealing material of the inorganic material include a transparent inorganic material, such as a low melting point glass.

As described above, the wavelength converter 1 preferably includes an inorganic material, and thus the sealing material 4 preferably includes an inorganic material. Preferably, zinc oxide (ZnO) is used as the inorganic material. This further enhances the heat dissipation of the phosphor, which prevents the output of the phosphor from decreasing due to temperature quenching and provides the light emitting device 10 that emits high output near-infrared light.

Figure 3:
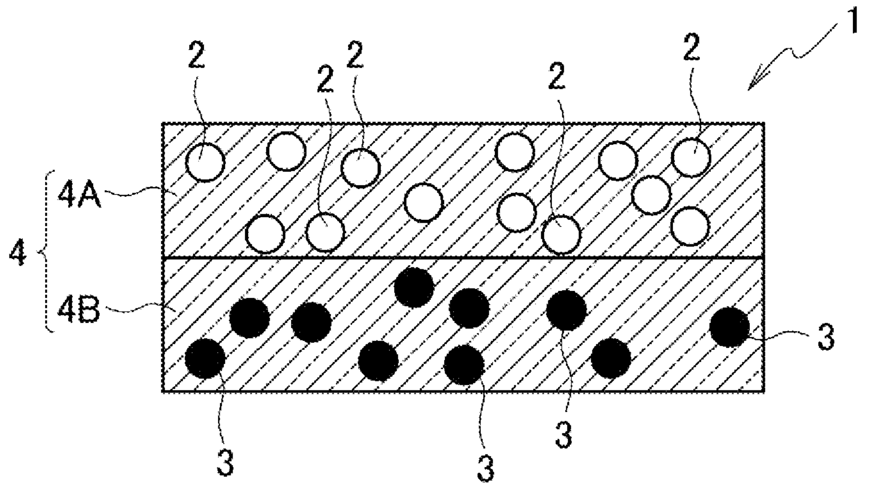
FIG. 3 is a schematic sectional view of another example of a wavelength converter.

FIG. 1 illustrates an example in which the first phosphor 2 and the second phosphor 3 are uniformly mixed and dispersed in a single layer of the sealing material 4. However, the wavelength converter 1 is not limited to such a configuration. As illustrated in FIG. 3, for example, the wavelength converter 1 may have a first sealing material 4A and a second sealing material 4B. The first phosphor 2 may be dispersed in the first sealing material 4A, and the second phosphor 3 may be dispersed in the second sealing material 4B. As illustrated in FIG. 3, the first sealing material 4A and the second sealing material 4B each may form a layer, and layers may be stacked to overlap each other. The first sealing material 4A and the second sealing material 4B may be formed of the same material or different materials.

Figure 4:
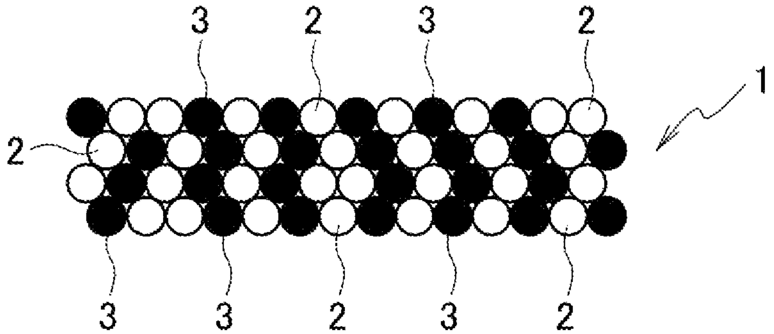
FIG. 4 is a schematic sectional view of another example of the wavelength converter.
Figure 5:
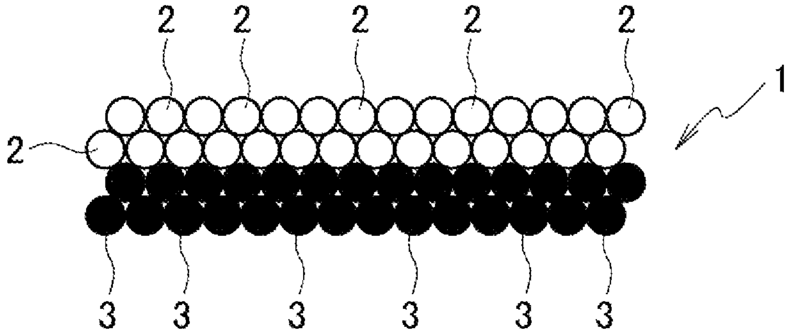
FIG. 5 is a schematic sectional view of another example of the wavelength converter.

As illustrated in FIGS. 4 and 5, the wavelength converter 1 may not use the sealing material 4. More specifically, as illustrated in FIG. 4, the wavelength converter 1 does not have the sealing material 4, and the first phosphor 2 and the second phosphor 3 may be uniformly mixed and dispersed. As illustrated in FIG. 5, the wavelength converter 1 does not have the sealing material 4, the first phosphor 2 and the second phosphor 3 may each form an aggregated layer, and layers may be stacked to overlap each other. In this case, the phosphor may be fixed to each other by using an organic or inorganic binder. The phosphor is fixable to each other by using the heating reaction of the phosphor. As the binder, a commonly used resin-based adhesive, ceramic fine particles, low melting point glass, or the like is usable. The wavelength converter 1 without using the sealing material 4 is made thin and thus is suitably used for the light emitting device 10.

Next, the operation of the light emitting device 10 according to the present embodiment is described. In the light emitting device 10 illustrated in FIG. 1, first, the primary light 6 emitted by the light source 5 is emitted to a front 1A of the wavelength converter 1. Most of the emitted primary light 6 enters the wavelength converter 1 from the front 1A of the wavelength converter 1 and passes through the wavelength converter 1, and a part of the emitted primary light 6 is reflected on the surface of the wavelength converter 1. The second phosphor 3 absorbs a part of the primary light 6 and converts it into the second wavelength-converted light 8, and the first phosphor 2 absorbs a part of the primary light 6 and/or a part of the second wavelength-converted light 8 and converts it into the first wavelength-converted light 7. Thus, the light emitting device 10 emits a light including the primary light 6, the first wavelength-converted light 7, and the second wavelength-converted light 8 from a back 1B of the wavelength converter 1, as output light.

Figure 6:
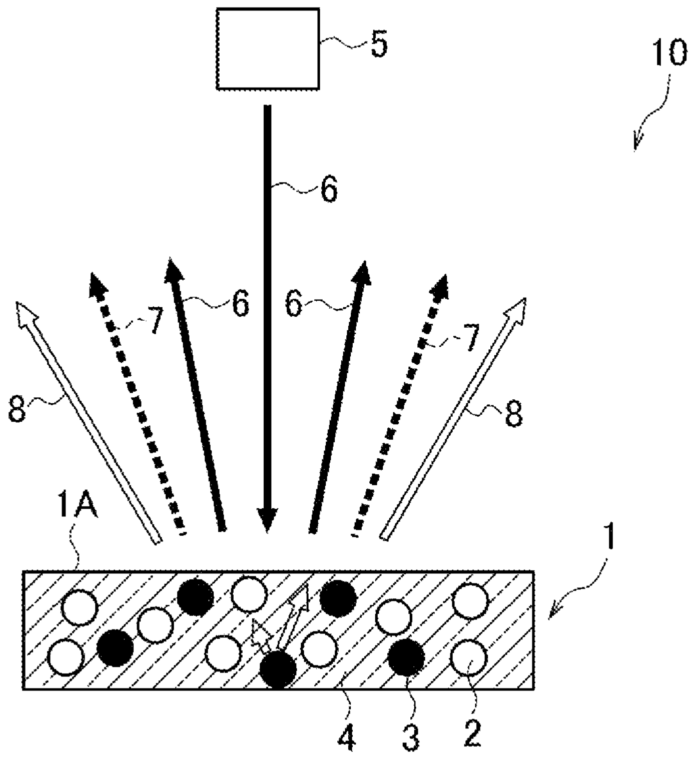
FIG. 6 is a schematic sectional view of another example of the light emitting device according to the present embodiment.

The light emitting device 10 is not limited to the configuration illustrated in FIG. 1, but may be the configuration illustrated in FIG. 6. In the light emitting device 10 illustrated in FIG. 6, first, the primary light 6 emitted by the light source 5 is emitted to the front 1A of the wavelength converter 1. Most of the emitted primary light 6 enters the wavelength converter 1 from the front 1A of the wavelength converter 1, and a part of the emitted primary light 6 is reflected on the surface of the wavelength converter 1. The second phosphor 3 absorbs a part of the primary light 6 and converts it into the second wavelength-converted light 8, and the first phosphor 2 absorbs a part of the primary light 6 and/or a part of the second wavelength-converted light 8 and converts it into the first wavelength-converted light 7. In this way, the light emitting device 10 emits a light including the primary light 6, the first wavelength-converted light 7, and the second wavelength-converted light 8 from the front 1A of the wavelength converter 1, as output light.

In the light emitting device 10 according to the present embodiment, the first wavelength-converted light 7 has the 1/10 afterglow time longer than that of the second wavelength-converted light 8. Therefore, the light emitting device 10 is capable of emitting alternately in time the first wavelength-converted light 7 including a large number of near-infrared fluorescent components with a long afterglow property and the second wavelength-converted light 8 including a large number of visible components with a short afterglow property. Therefore, as described above, the light emitting device 10 emits near-infrared light and visible light to obtain high-contrast observation results.

The above-described light emitting device 10 may be used for medical purposes. That is, the light emitting device 10 may be a medical light emitting device. In other words, the light emitting device 10 may be a medical illumination device. Such a light emitting device 10 is advantageous in diagnosing disease state because it achieves the coexistence of normal observation and special observation as described above.

The light emitting device 10 may be used for optical coherence tomography (OCT) or the like. However, preferably, the light emitting device 10 is used for either a fluorescence imaging method or photodynamic therapy. The light emitting device 10 used in these methods is a light emitting device for a medical system using a drug, such as a fluorescent drug or a photosensitive drug. These methods are a promising medical technology with a wide range of applications and are highly practical. The light emitting device 10 illuminates the inside of the living body with a broad near-infrared high-output light through the "living body window" and makes the fluorescent drug or photosensitive drug taken into the living body fully functional, which is expected to have a large therapeutic effect.

The fluorescence imaging method is a method of observing a lesion by administering a fluorescent drug that selectively binds to the lesion, such as a tumor, to a subject, exciting the fluorescent drug with a specific light, and detecting and imaging fluorescence emitted from the fluorescent drug with an image sensor. The fluorescence imaging method makes it possible to observe lesions that are difficult to observe using only general illumination. As the fluorescent drug, a drug that absorbs excitation light in the near-infrared range, and emits fluorescence in the near-infrared range and at a wavelength longer than the excitation light is usable. Examples of the fluorescent drug used include at least one selected from the group consisting of indocyanine green (ICG), a phthalocyanine-based compound, a talaporfin sodium-based compound, and a dipicolylcyanine (DIPCY)-based compound.

The photodynamic therapy is a treatment method of administering a photosensitive drug that selectively binds to a target biological tissue to a subject and irradiating the photosensitive drug with near-infrared light. When the photosensitive drug is irradiated with the near-infrared light, the photosensitive drug generates active oxygen, which is usable to treat lesions, such as tumors or infections. Examples of the photosensitive drug used include at least one selected from the group consisting of a phthalocyanine-based compound, a talaporfin sodium-based compound, and a porfimer sodium-based compound.

The light emitting device 10 according to the present embodiment may be used as a light source for a sensing system or an illumination system for a sensing system. With the light emitting device 10, an orthodox light receiving element having light receiving sensitivity in the near-infrared wavelength range may be used to configure a high-sensitivity sensing system. This provides a light emitting device that facilitates miniaturization of the sensing system and broadening of the sensing range.

[Healthcare System]

Next, a medical system including the above-described light emitting device 10 is described. Specifically, as an example of the medical system, an endoscope 11 provided with the light emitting device 10 and an endoscope system 100 using the endoscope 11 are described with reference to FIGS. 7 and 8.

(Endoscope)

Figure 7:
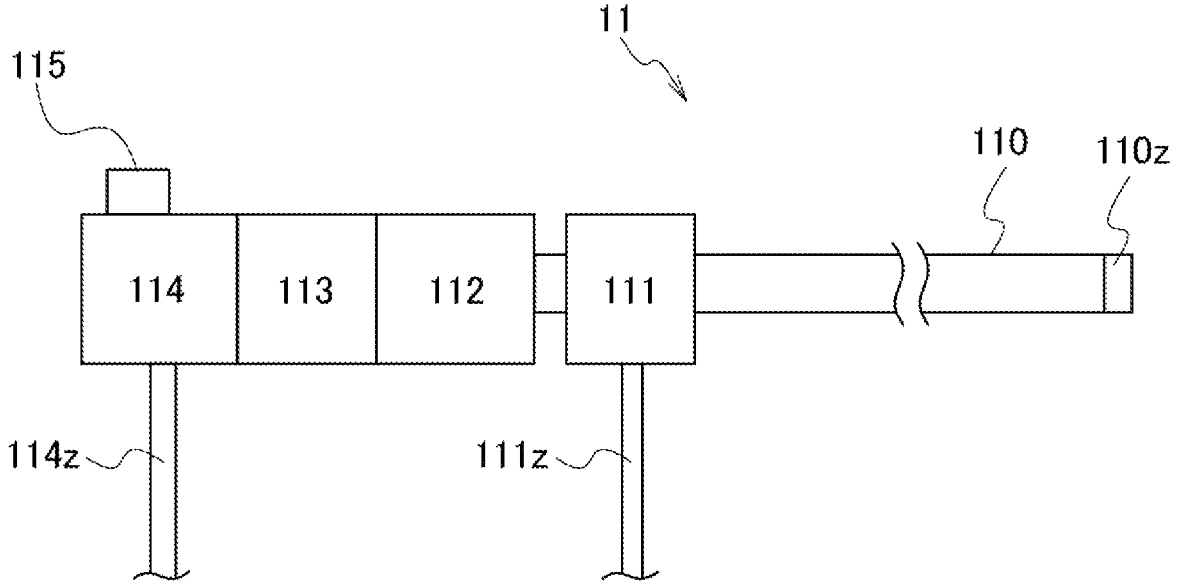
FIG. 7 is a schematic diagram illustrating a configuration of an endoscope according to a present embodiment.

As illustrated in FIG. 7, the endoscope 11 according to the present embodiment includes the above-described light emitting device 10. The endoscope 11 includes a scope 110, a light source connector 111, a mount adapter 112, a relay lens 113, a camera head 114, and an operation switch 115.

The scope 110 is an elongated light guide member capable of guiding light from end to end and is inserted into the body when in use. The scope 110 includes an imaging window 110*z* at its tip. For the imaging window 110*z*, an optical material, such as optical glass or optical plastic, is used. The scope 110 includes an optical fiber for guiding light introduced from the light source connector 111 to the tip, and an optical fiber for transmitting an optical image that enters through the imaging window 110*z*.

The light source connector 111 introduces illumination light emitted to a diseased part and the like in the body from the light emitting device 10. In the present embodiment, the illumination light includes visible light and near-infrared light. The light introduced into the light source connector 111 is guided to the tip of the scope 110 through the optical fiber to be emitted to a diseased part and the like in the body from the imaging window 110*z*. As illustrated in FIG. 7, the light source connector 111 is provided with a transmission cable 111*z* for guiding illumination light from the light emitting device 10 to the scope 110. The transmission cable 111*z* may include an optical fiber.

The mount adapter 112 is a member for mounting the scope 110 on the camera head 114. Various scopes 110 are detachably mountable on the mount adapter 112.

The relay lens 113 converges the optical image transmitted through the scope 110 on the imaging surface of the image sensor. The relay lens 113 may be moved in accordance with the operation amount of the operation switch 115 to perform focus adjustment and magnification adjustment.

The camera head 114 includes a color separation prism inside. The color separation prism separates the light converged by the relay lens 113 into four colors of R light (red light), G light (green light), B light (blue light), and IR light (near-infrared light). The color separation prism includes, for example, a light transmitting member, such as glass.

The camera head 114 further includes an image sensor as a detector inside. For example, four image sensors are provided, and each of the four image sensors converts an optical image formed on an imaging surface into an electric signal. The image sensor is not limited, but at least one of CCD (Charge Coupled Device) or CMOS (Complementary Metal Oxide Semiconductor) is usable. The four image sensors are dedicated sensors for receiving light of the IR component (near-infrared component), the B component (blue component), the R component (red component), and the G component (green component), respectively.

The camera head 114 may have a color filter inside instead of the color separation prism. The color filter is provided on the imaging surface of the image sensor. For example, four color filters are provided, and the four color filters receive the light converged by the relay lens 113 and selectively transmit R light (red light), G light (green light), B light (blue light), and IR light (near-infrared light), respectively.

Preferably, the color filter for selectively transmitting IR light includes a barrier film for cutting the reflection component of near-infrared light (IR light) included in the illumination light. This enables only the fluorescence composed of IR light emitted from a fluorescent drug, such as ICG, to form an image on the imaging surface of the image sensor for IR light. Therefore, the diseased part luminous with the fluorescent drug is easily observed clearly.

As illustrated in FIG. 7, a signal cable 114*z* is connected to the camera head 114 to transmit an electric signal from the image sensor to a CCU 12 described later.

In the endoscope 11 having such a configuration, light from a subject is guided to the relay lens 113 through the scope 110 and is further transmitted through the color separation prism in the camera head 114 to form images on the four image sensors.

(Endoscope System)

Figure 8:
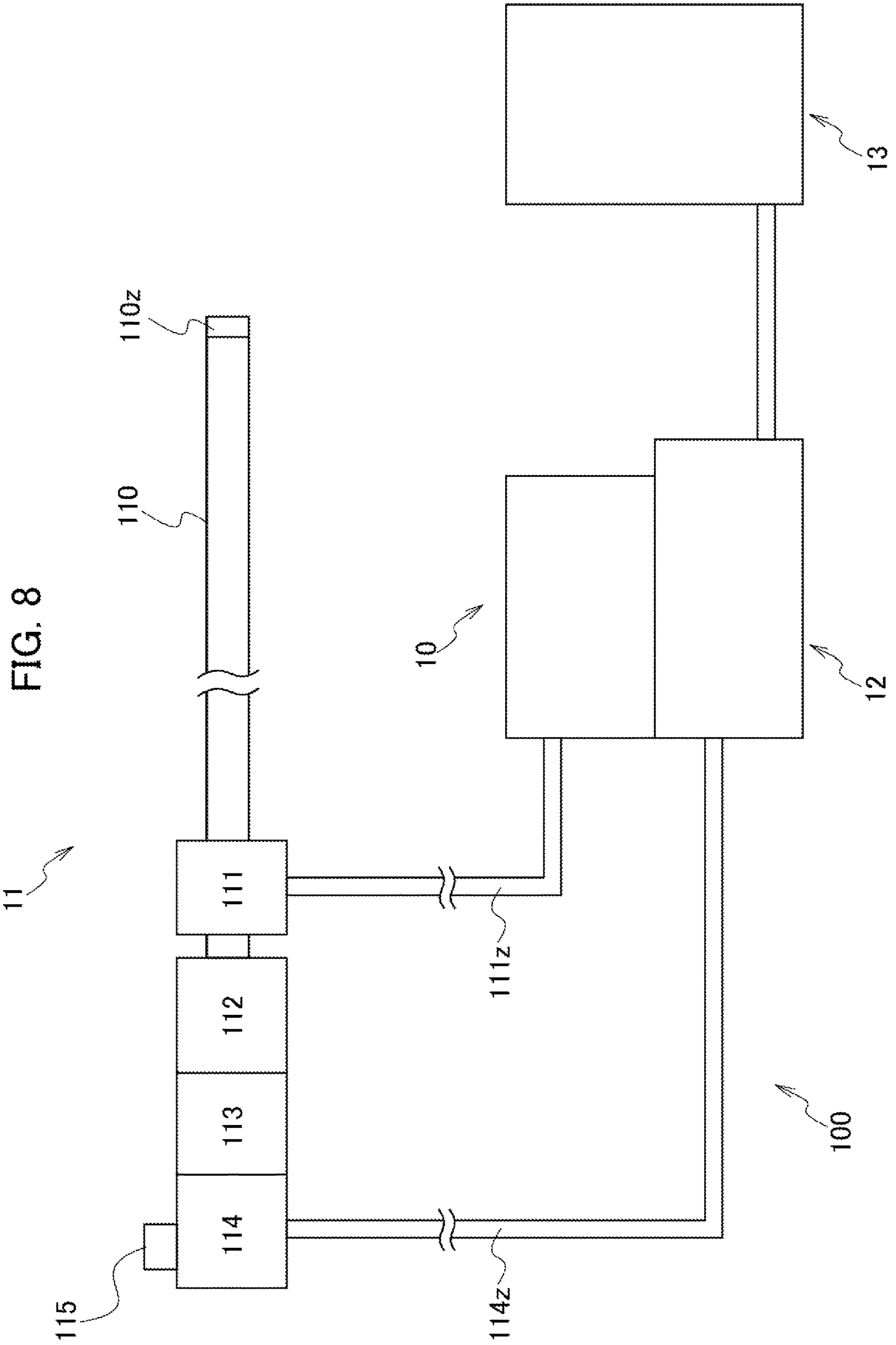
FIG. 8 is a schematic diagram illustrating a configuration of an endoscope system according to the present embodiment.

As illustrated in FIG. 8, the endoscope system 100 includes the endoscope 11 for imaging the inside of a subject, a CCU (Camera Control Unit) 12, and a display device 13 such as a display.

The CCU 12 includes at least an RGB signal processing unit, an IR signal processing unit, and an output unit. The CCU 12 executes a program stored in the internal or external memory of the CCU 12 to realize the respective functions of the RGB signal processing unit, the IR signal processing unit, and the output unit.

The RGB signal processing unit converts the R component, G component, and B component electrical signals from the image sensors into video signals that are displayable on the display device 13 and outputs the video signals to the output unit. The IR signal processing unit converts the IR component electrical signal from the image sensor into a video signal and outputs the video signal to the output unit.

The output unit outputs at least one of the video signals of respective RGB color components or the video signal of the IR component to the display device 13. For example, the output unit outputs video signals on the basis of either a simultaneous output mode or a superimposed output mode.

In the simultaneous output mode, the output unit simultaneously outputs the RGB image and the IR image on separate screens. The simultaneous output mode enables the diseased part to be observed by comparing the RGB image and the IR image on the separate screens. In the superimposed output mode, the output unit outputs a composite image in which the RGB image and the IR image are superimposed. The superimposed output mode enables the diseased part luminous with the ICG to be clearly observed, for example in the RGB image.

The display device 13 displays an image of an object, such as a diseased part, on a screen on the basis of video signals from the CCU 12. In the simultaneous output mode, the display device 13 divides the screen into multiple screens and displays the RGB image and the IR image side by side on each screen. In the superimposed output mode, the display device 13 displays a composite image in which an RGB image and an IR image are superimposed on each other on a single screen.

Next, functions of the endoscope 11 and the endoscope system 100 according to the present embodiment are described. When a subject is observed using the endoscope system 100, first, indocyanine green (ICG) as a fluorescent substance is administered to the subject. As a result, ICG accumulates at a site of lymph, tumor, or the like (diseased part).

Next, visible light and near-infrared light are introduced from the light emitting device 10 to the light source connector 111 through the transmission cable 111*z*. The light introduced into the light source connector 111 is guided to the tip side of the scope 110 and projected from the imaging window 110*z* to be emitted to the diseased part and the periphery of the diseased part. The light reflected from the diseased part and the like and the fluorescence emitted from the ICG are guided to the rear end side of the scope 110 through the imaging window 110*z* and the optical fiber, converged by the relay lens 113 to enter into the color separation prism inside the camera head 114.

In the color separation prism, among the incident light, the light of the IR component separated by the IR separation prism is imaged as an optical image of an infrared component by the IR light image sensor. The light of the R component separated by the red separation prism is imaged as an optical image of the red component by the R light image sensor. The light of the G component separated by the green separation prism is imaged as an optical image of the green component by the G light image sensor. The light of the B component separated by the blue separation prism is imaged as an optical image of the blue component by the B light image sensor.

The electrical signal of the IR component converted by the IR light image sensor is converted into a video signal by the IR signal processing unit in the CCU 12. The electric signals of the R component, G component, and B component converted by the RGB light image sensors are converted into respective video signals by the RGB signal processing unit in the CCU 12. The image signal of the IR component, and the image signals of the R component, G component, and B component in synchronization with each other are output to the display device 13.

When the simultaneous output mode is set in the CCU 12, the RGB image and the IR image are simultaneously displayed on two screens on the display device 13. When the superimposed output mode is set in the CCU 12, a composite image in which the RGB image and the IR image are superimposed is displayed on the display device 13.

As described above, the endoscope 11 according to the present embodiment includes the light emitting device 10. Therefore, by efficiently exciting the fluorescent drug to emit light using the endoscope 11, the diseased part is clearly observed.

Preferably, the endoscope 11 according to the present embodiment further includes a detector for detecting fluorescence emitted from a fluorescent drug that has absorbed the first wavelength-converted light 7. By providing the endoscope 11 with the detector for detecting fluorescence emitted from a fluorescent drug in addition to the light emitting device 10, the diseased part is specified only by the endoscope 11. This makes it possible to perform medical examination and treatment with less burden on the patient, since there is no need to open the abdomen wide to identify the diseased part as in the conventional method. This also enables the doctor using the endoscope 11 to accurately identify the diseased part, which improves the efficiency of treatment.

As described above, preferably, the medical system is used for either the fluorescence imaging method or photodynamic therapy. The medical system used in these methods is a promising medical technology with a wide range of applications and is highly practical. The medical system illuminates the inside of the living body with a broad near-infrared high-output light through the "living body window" and makes the fluorescent drug or photosensitive drug taken into the living body fully functional, which is expected to have a large therapeutic effect. Further, such a medical system uses the light emitting device 10 having a relatively simple configuration, which is advantageous in reducing the size and the cost.

[Electronic Apparatus]

Next, an electronic apparatus according to the present embodiment is described. The electronic apparatus according to the present embodiment includes a light emitting device 10. As described above, the light emitting device 10 is expected to have a large therapeutic effect, and it is easy to miniaturize the sensing system. Since the electronic apparatus according to the present embodiment uses the light emitting device 10, when it is used for a medical device or a sensing device, a large therapeutic effect, miniaturization of the sensing system, and the like are expected.

The electronic apparatus includes, for example, the light emitting device 10, and a light receiving element. The light receiving element is, for example, a sensor, such as an infrared sensor for detecting light in a near-infrared wavelength range. The electronic apparatus may be any of an information recognition device, a sorting device, a detection device, or an inspection device. As described above, these devices also facilitate miniaturization of the sensing system and broadening of the sensing range.

The information recognition device is, for example, a driver support system that recognizes the surrounding situation by detecting reflected components of emitted infrared rays.

The sorting device is, for example, a device that sorts an irradiated object into predetermined categories by using the difference in infrared light components between the irradiation light and reflected light reflected by the irradiated object.

The detection device is, for example, a device that detects a liquid. Examples of liquids include water, and flammable liquids that are prohibited from being transported in aircraft. Specifically, the detection device may be a device for detecting moisture adhering to glass, and moisture absorbed by an object, such as sponge or fine powder. The detection device may visualize the detected liquid. Specifically, the detection device may visualize the distribution information of the detected liquid.

The inspection device may be any of a medical inspection device, an agricultural and livestock inspection device, a fishery inspection device, or an industrial inspection device. These devices are useful for inspecting an inspection object in each industry.

The medical inspection device is, for example, an examination device that examines the health condition of a human or non-human animal. Non-human animals are, for example, domestic animals. The medical inspection device is, for example, a device used for a biological examination, such as a fundus examination or a blood oxygen saturation examination, and a device used for examination of an organ, such as a blood vessel or an organ. The medical inspection device may be a device for examining the inside of a living body or a device for examining the outside of a living body.

The agricultural and livestock inspection device is, for example, a device for inspecting agricultural and livestock products including agricultural products and livestock products. Agricultural products may be used as foods, for example, fruits and vegetables, or cereals, or as fuels, such as oils. Livestock products include, for example, meat and dairy products. The agricultural and livestock inspection device may be a device for non-destructively inspecting the inside or outside of the agricultural and livestock products. Examples of the agricultural and livestock inspection device includes a device for inspecting the sugar content of vegetables and fruits, a device for inspecting the acidity of vegetables and fruits, a device for inspecting the freshness of vegetables and fruits by the visualization of leaf veins, a device for inspecting the quality of vegetables and fruits by the visualization of wounds and internal defects, a device for inspecting the quality of meat, and a device for inspecting the quality of processed foods processed with milk, meat, or the like as raw materials.

The fishery inspection device is, for example, a device for inspecting the flesh quality of fish, such as tuna, or a device for inspecting the presence or absence of the contents in shells of shellfish.

The industrial inspection device is, for example, a foreign matter inspection device, a content inspection device, a condition inspection device, or a structure inspection device.

Examples of the foreign matter inspection device include a device for inspecting foreign matter in a liquid contained in a container, such as a beverage or a liquid medicine, a device for inspecting foreign matter in a packaging material, a device for inspecting foreign matter in a printed image, a device for inspecting foreign matter in a semiconductor or an electronic component, a device for inspecting foreign matter, such as residual bone in food, dust, or machine oil, a device for inspecting foreign matter in processed food in a container, and a device for inspecting foreign matter in medical devices, such as adhesive plasters, medical and pharmaceutical products, or quasi-drugs.

Examples of the content inspection device include a device for inspecting the content of a liquid contained in a container, such as a beverage or a liquid medicine, a device for inspecting the content of a processed food contained in a container, and a device for inspecting the content of asbestos in building materials.

Examples of the state inspection device include a device for inspecting packaging state of a packaging material, and a device for inspecting printing state of a packaging material.

Examples of the structure inspection device include an internal non-destructive inspection device and an external non-destructive inspection device for a composite member or a composite component, such as a resin product. A specific example of the resin product is, for example, a metal brush with a part of metal wire embedded in the resin, and the inspection device inspects the bonding state of the resin and the metal.

The electronic apparatus may use color night vision technology. Color night vision technology uses a correlation of reflection intensity between visible light and infrared rays to colorize an image by assigning infrared rays to RGB signals for each wavelength. According to the color night vision technology, a color image is obtained only by infrared rays, and it is particularly suitable for a security device.

As described above, the electronic apparatus includes the light emitting device 10. When the light emitting device 10 includes a power source, a light source 5, a first phosphor 2, and a second phosphor 3, it is not necessary to accommodate all of them in one housing. Therefore, the electronic apparatus according to the present embodiment provides a highly accurate and compact inspection method, or the like, with excellent operability.

[Inspection Method]

Next, an inspection method according to the present embodiment is described. As described above, the electronic apparatus including the light emitting device 10 is also usable as an inspection device. That is, the light emitting device 10 is usable in the inspection method according to the present embodiment. This provides a highly accurate and compact inspection method with excellent operability.

EXAMPLES

The light emitting device according to the present embodiment is described below in more detail with reference to examples, but the present embodiment is not limited thereto.

[Preparation of Phosphor]

(First Phosphor)

A first phosphor was synthesized using a preparation method utilizing a solid phase reaction. The $Cr^{3+}$-activated phosphor used in the first phosphor is an oxide phosphor represented by a formula: $Gd_3(Ga_{0.97}Cr_{0.03})_2Ga_3O_{12}$. In synthesizing the first phosphor, the following compound powders were used as main raw materials.

- Gadolinium oxide ($Gd_2O_3$): purity 3N, Wako Pure Chemical Corporation
- Gallium oxide ($Ga_2O_3$): purity 4N, Wako Pure Chemical Corporation
- Chromium oxide ($Cr_2O_3$): Purity 3N, Kojundo Chemical Laboratory Co., Ltd.

First, the above-described raw materials were weighed to obtain a compound of a stoichiometric composition $Gd_3(Ga_{0.97}Cr_{0.03})_2Ga_3O_{12}$. The weighed raw materials were then put into a beaker containing pure water and stirred with a magnetic stirrer for 1 hour. Thus, a slurry-like mixed raw material of the pure water and raw materials was obtained. Then, the slurry-like mixed raw material was dried entirely using a dryer. The mixed raw material after drying was pulverized using a mortar and a pestle to obtain a calcined raw material.

The above-described calcined raw material was transferred to a small alumina crucible and calcined in air at 1400° C. to 1500° C. for 1 hour in a box-type electric furnace to obtain the phosphor of this example. The temperature rise and fall rate was set at 400° C./h. The body color of the obtained phosphor was light green.

The phosphor obtained by calcination was crushed for several minutes using an alumina mortar and pestle. Then, classification was performed using a sieve (mesh opening: 25 μm) to obtain powder of the first phosphor.

(Second Phosphor)

A commercially available YAG phosphor ($Y_3Al_2Al_3O_{12}$:Ce) was obtained as a second phosphor. In consideration of the fluorescence peak wavelength and the like, the chemical composition of the YAG phosphor is estimated to be $(Y_{0.995}Ce_{0.005})_3Al_2Al_3O_{12}$.

[Evaluation]

(Crystal Structure Analysis)

The crystal structures of the first phosphor and the second phosphor were evaluated using an X-ray diffraction apparatus (X'Pert PRO; manufactured by Spectris Co., Ltd., PANalytical).

As a result of evaluation, it was found that the first and second phosphors were mainly made from compounds with a garnet crystal structure, although the details are omitted. That is, both the first phosphor and the second phosphor were found to be garnet phosphors.

(Fluorescence Spectrum)

Next, wavelength converters including the first phosphor and the second phosphor were prepared, and the fluorescence properties were evaluated. Specifically, a phosphor paste was prepared by mixing the first phosphor powder, the second phosphor powder, and the sealing material (polysilsesquioxane manufactured by Konishi Chemical Ind. Co., Ltd.) using a mortar and pestle so that the filling ratio of the phosphor was 40 vol %. This phosphor paste was screen-printed (mesh opening 74 μm; 200 mesh, size 7.8 mm) on the surface of a dichroic mirror of a sapphire substrate (9 mm×9 mm×5 mm thick) that had the dichroic mirror on one surface and an AR coating on the other surface. Then, the sealing material was cured by heat treatment at 200° C. for 2 hours to prepare a wavelength converter.

Next, the wavelength converter was placed at the center of an integrating sphere, the phosphor was irradiated with a blue laser light having a peak wavelength of 450 nm, and a fluorescence spectrum was measured by a multichannel spectrometer. The blue LD light was converted into a pulsed light having a frequency of 100 Hz and a duty ratio of 1%.

Figure 9:
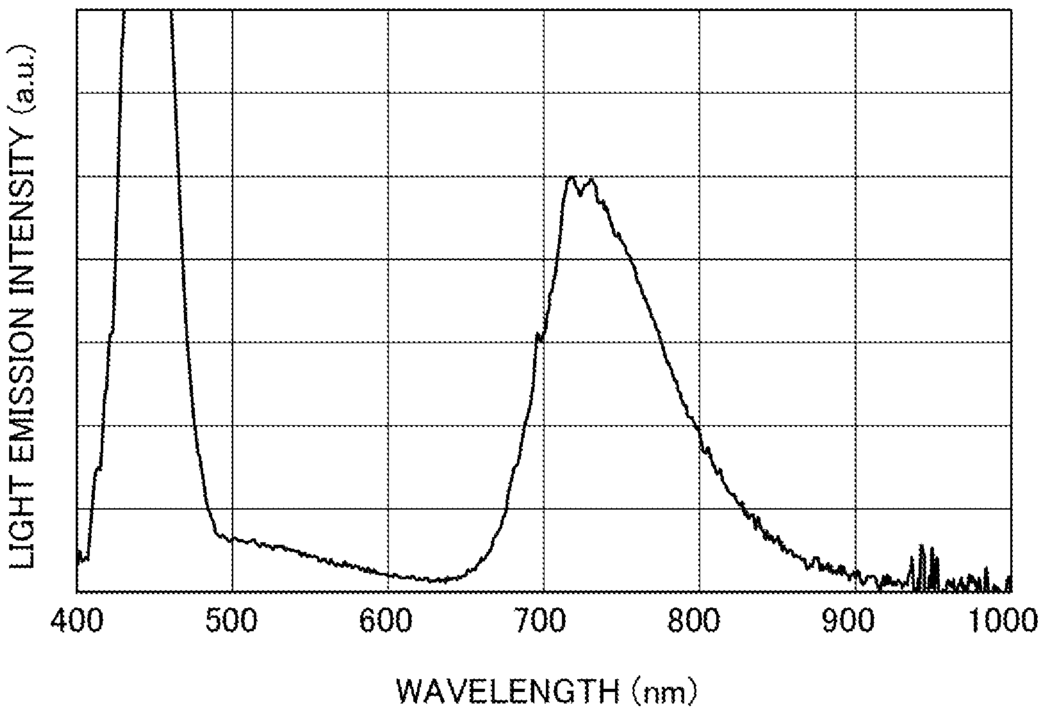
FIG. 9 is a fluorescence spectrum of fluorescence emitted by a first phosphor according to an example.

FIG. 9 illustrates the fluorescence spectrum of the first phosphor. The sharp spectrum around 450 nm is the reflected component of the excitation light. The fluorescence spectrum of the first phosphor was formed from a broad spectrum determined to be attributed to the d-d transition of $Cr^{3+}$. The fluorescence spectrum of the first phosphor had a light component over the entire wavelength range of 700 nm or more to 800 nm or less. In addition, the peak wavelength of the fluorescence spectrum of the first phosphor was 718 nm.

Figure 10:
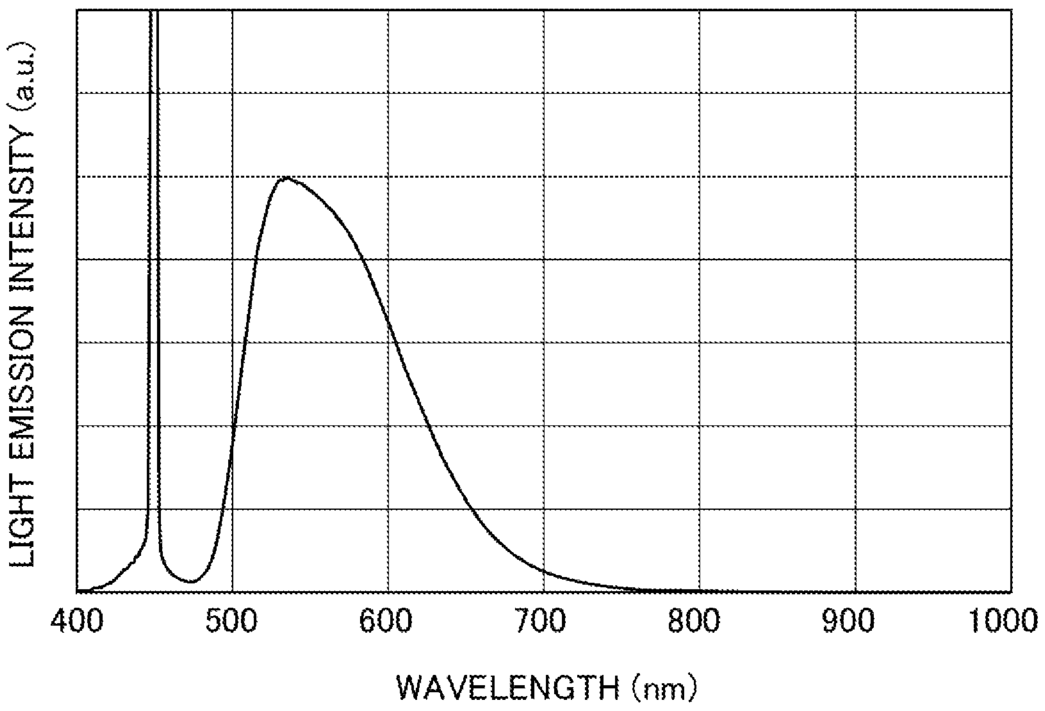
FIG. 10 is a fluorescence spectrum of fluorescence emitted by a second phosphor according to the example.

FIG. 10 illustrates the fluorescence spectrum of the second phosphor. The sharp spectrum around 450 nm is the reflected component of the excitation light. The fluorescence spectrum of the second phosphor was formed from a broad spectrum determined to be attributed to the $5d^1 \rightarrow 4f^1$ transition of $Ce^{3+}$. The fluorescence spectrum of the second phosphor had a fluorescence peak within a wavelength range of 380 nm or more to less than 700 nm. Specifically, the peak wavelength of the fluorescence spectrum of the second phosphor was 535 nm.

(Afterglow Time)

The 1/10 afterglow time of the first phosphor and the second phosphor was measured using a Quantaurus-Tau compact fluorescence lifetime measuring device (C11367 manufactured by Hamamatsu Photonics K.K.).

Table 1 shows the 1/10 afterglow time of each of the first phosphor and second phosphor. The 1/10 afterglow time of the first phosphor and the second phosphor were 383 μs and 135 ns, respectively.

TABLE 1

| | First phosphor | Second phosphor |
|---|---|---|
| Afterglow time | 383 μs | 135 ns |

From the above results, a fluorescence spectrum having a light component over the entire wavelength range of 700 nm or more to 800 nm or less, and a fluorescence spectrum having a fluorescence peak within the wavelength range of 380 nm or more to less than 700 nm were obtained. Considering the afterglow time of the first phosphor and the second phosphor, it can be said that fluorescence having a light component over the entire wavelength range of 700 nm or more to 800 nm or less, and fluorescence having a fluorescence peak within the wavelength range of 380 nm or more to less than 700 nm are emitted alternately in time.

For example, suppose that the wavelength converter, which is a mixture of the first phosphor and the second phosphor, is excited by a pulsed laser light source having a frequency of 1000 Hz and a duty ratio of 60% (light source from which laser light is emitted for 600 μs and laser light is not emitted for 400 μs out of 1000 μs). Then, the second phosphor immediately emits fluorescence, and after about 100 ns (0.1 μs), the light emission intensity becomes about 1/10. In contrast, the first phosphor emits fluorescence later than the second phosphor, and becomes a light source having the light emission intensity of about 1/10 after about 400 μs. That is, it can be said that the above-described light source mainly emits fluorescence having a fluorescence peak in a wavelength range of 380 nm or more to less than 700 nm for 600 μs during which the laser light is emitted, out of 1000 μs. In contrast, it can be said that fluorescence having a light component over the entire wavelength range of 700 nm or more to 800 nm or less is mainly emitted for 400 μs during which the laser light is not emitted.

Note that the time period during which fluorescence having a fluorescence peak in the wavelength range of 380 nm or more to less than 700 nm is mainly emitted and the time period during which fluorescence having a light component over the entire wavelength range of 700 nm or more to 800 nm or less is mainly emitted are adjustable to arbitrary values. Specifically, these time periods are adjustable to arbitrary values by controlling the frequency or duty ratio of the pulsed laser light, or the afterglow time of the phosphor.

The entire contents of Japanese Patent Application No. 2019-082916 (filed Apr. 24, 2019) are incorporated herein by reference.

Although the contents of the present embodiment have been described in accordance with the examples above, it is obvious to those skilled in the art that the present embodiment is not limited to these descriptions, and that various modifications and improvements are possible.

INDUSTRIAL APPLICABILITY

In accordance with the present disclosure, there is provided a light emitting device that emits near-infrared light and visible light to obtain a high-contrast observation result, and a medical system, an electronic apparatus, and an inspection method using the light emitting device.

REFERENCE SIGNS LIST

1 Wavelength converter
2 First phosphor
3 Second phosphor
5 Light source
6 Primary light
7 First wavelength-converted light
8 Second wavelength-converted light
10 Light emitting device

The invention claimed is:

1. A system, comprising:
a light emitting device; and
a near-infrared light image sensor, wherein
the light emitting device comprises:
a light source configured to emit a primary light;
a first phosphor that absorbs the primary light and converts the primary light into a first wavelength-converted light having a wavelength longer than that of the primary light; and
a second phosphor that absorbs the primary light and converts the primary light into a second wavelength-converted light having a wavelength longer than that of the primary light,
the first wavelength-converted light is a fluorescence having a light component over an entire wavelength range of 700 nm or more to 800 nm or less;
the second wavelength-converted light is a fluorescence having a peak where a fluorescence intensity shows a maximum value in a wavelength range of 380 nm or more to less than 700 nm;
the first wavelength-converted light has a 1/10 afterglow time longer than that of the second wavelength-converted light;
the light emitting device emits the first wavelength-converted light and the second wavelength-converted light alternately in time such that a fluorescence emitted from an irradiated object excited by the first wavelength-converted light and having a longer wavelength than the first wavelength-converted light is detected by the near-infrared light image sensor while an intensity of the second wavelength-converted light is smaller than an intensity of the first wavelength-converted light after the primary light is no longer emitted by the light source;
the first phosphor is activated with $Cr^{3+}$; and
a fluorescence spectrum of the first wavelength-converted light has a peak where a fluorescence intensity shows a maximum value in a wavelength range exceeding 720 nm.

2. The system according to claim 1, wherein the first wavelength-converted light and the second wavelength-converted light have a 1/10 afterglow time difference exceeding 50 μs.

3. The system according to claim 1, wherein the primary light is a laser light.

4. The system according to claim 1, wherein the primary light is a continuous pulsed light.

5. The system according to claim 4, wherein an extinction time of the continuous pulsed light is longer than the 1/10 afterglow time of the second wavelength-converted light.

6. The system according to claim 1, wherein the first phosphor is activated with a transition metal ion.

7. The system according to claim 1, wherein the second phosphor is activated with at least one of $Ce^{3+}$ or $Eu^{2+}$.

8. The system according to claim 1, wherein the second wavelength-converted light has a correlated color temperature of 2500 K or more and less than 7000 K.

9. The system according to claim 1, wherein the light emitting device is a light source for a sensing system, or an illumination system for a sensing system.

10. The system according to claim 1, wherein the light emitting device is used in either a fluorescence imaging method or a photodynamic therapy.

11. A medical system, comprising:
the system according to claim 1.

12. An electronic apparatus, comprising:
the system according to claim 1.

13. The electronic apparatus according to claim 12, wherein the electronic apparatus is any one of an information recognition device, a sorting device, a detection device, or an inspection device.

14. The electronic apparatus according to claim 13, wherein the inspection device is any one of a medical inspection device, an agricultural and livestock inspection device, a fishery inspection device, or an industrial inspection device.

15. An inspection method, comprising:
using the system according to claim 1.

16. The system according to claim 1, wherein the primary light is a continuous pulsed light that turns on and off repeatedly.

17. The system according to claim 1, wherein the irradiated object is a fluorescent drug.

18. The system according to claim 1, wherein the first wavelength converted light has a light component over the entire wavelength range of 750 nm or more to 800 nm or less.

19. The system according to claim 1, wherein a spectrum of a primary light emitted by the light source has a peak where the intensity shows a maximum value in a range of 430 nm or more to less than 500 nm.

* * * * *